United States Patent
Blasing

(10) Patent No.: US 6,404,490 B2
(45) Date of Patent: Jun. 11, 2002

(54) METHOD FOR DETECTING AND LOCALIZING DIFFUSE REFLECTING COATINGS SITUATED ON A TRANSLUCENT PANE

(75) Inventor: Frank Blasing, Werl (DE)

(73) Assignee: Leopold Kostal GmbH & Co. KG, Ludenscheid (DE)

(*) Notice: Subject to any disclaimer, the term of this patent is extended or adjusted under 35 U.S.C. 154(b) by 0 days.

(21) Appl. No.: 09/881,078

(22) Filed: Jun. 13, 2001

Related U.S. Application Data

(63) Continuation of application No. PCT/EP99/09944, filed on Dec. 15, 1999.

(30) Foreign Application Priority Data

Dec. 17, 1998 (DE) .......................................... 198 58 316

(51) Int. Cl.[7] .............................................. G01N 21/00
(52) U.S. Cl. .............................. 356/239.8; 250/227.25; 318/483
(58) Field of Search ........................... 356/239.1, 239.2, 356/239.3, 239.5, 239.7, 239.8, 237.1; 315/80, 83, 82; 318/483, 480; 15/DIG. 15; 340/580, 602, 600; 250/339.11, 341.8, 227.25; 73/170.17

(56) References Cited

U.S. PATENT DOCUMENTS

| | | | |
|---|---|---|---|
| 4,676,638 A | * 6/1987 | Yasuda | 356/237 |
| 4,867,561 A | 9/1989 | Fujii et al. | |
| 4,956,591 A | * 9/1990 | Schierbeek et al. | 318/483 |
| 5,313,072 A | * 5/1994 | Vachss | 250/573 |
| 5,459,330 A | * 10/1995 | Venaille et al. | 250/559.45 |
| 6,020,704 A | * 2/2000 | Buschur | 318/483 |

FOREIGN PATENT DOCUMENTS

| | | | |
|---|---|---|---|
| DE | 2420594 | * 6/1975 | |
| WO | WO 97/29926 | 2/1996 | |

\* cited by examiner

Primary Examiner—Hoa Q. Pham
(74) Attorney, Agent, or Firm—Brooks & Kushman, P.C.

(57) ABSTRACT

The invention relates to a method and device for detecting and localizing diffuse-reflecting coatings situated on a translucent pane. The aim of the invention is to make it possible to detect any diffuse-reflecting coatings in a non-contacting manner and to differentiate between coatings situated on the pane surface facing the sensor and those situated on the pane surface facing away from the sensor. To this end an image of an object is captured by a recording unit forming part of the device by positioning the pane in the optical path between the object and recording unit, after which the image information obtained is evaluated accordingly.

6 Claims, 3 Drawing Sheets

METHOD FOR DETECTING AND LOCALIZING DIFFUSE REFLECTING COATINGS SITUATED ON A TRANSLUCENT PANE

CROSS-REFERENCE TO RELATED APPLICATIONS

This is a continuation of International Application PCT/EP99/09944, with an international filing date of Dec. 15, 1999.

TECHNICAL FIELD

The invention has as its object a method for detecting the presence and the relative position of a diffuse reflecting coating, such as a film of moisture, on the surface of a translucent medium and a device for implementing the method.

Used, e.g., in vehicle windshields, such a method can be seen as the central function of a system for determining the degree of visibility.

BACKGROUND ART

The methods known until now for this purpose are based primarily on sensors that detect a film of moisture on a surface by means of a capacitive or resistive operating principle and that must be thermally coupled to said surface in order to achieve the same coating behavior as the surface being monitored.

Thus, e.g., a circuit arrangement for measuring moisture on the windshield of a vehicle is disclosed in DE 44 28 111 A1, in which the resistance between electrodes on the windshield which are in thermal contact with it is measured.

Detection of other coatings than those caused by moisture and detection of coatings on the surface opposite the sensor cannot be realized with methods of this previously known type.

In addition, a device and a method for detecting the presence and the relative position of coatings on a translucent pane are known from U.S. Pat. No. 4,867,561. Here, an optical sensor array with light from various light sources is applied, wherein these lights sources are arranged in two rows in order to be able to focus light reflected at various boundary surfaces of the pane uniformly on the sensor array. The presence of coatings is evaluated by means of the intensity of the light reflections caused by the various light sources, wherein, in order to normalize the absolute intensities, a region of sensor arrays is included that are not assigned to any light source.

Because of the number of light sources used in this method, both the device and the method are very expensive. Thus, the light sources involve a significant component cost, not only because of the number of light sources, but also because light sources must be chosen that generate approximately equal light intensities under equal power in order for the method based on intensity values to be implemented. Otherwise, the method must provide for a balancing of light sources of unequal intensity by individual adjustment of power to the light sources.

SUMMARY OF THE INVENTION

Starting from the state of the art, the present invention is based on the problem of providing a device and method with which, despite its lower cost, is able to detect and localize any diffuse reflecting coating without contact and thus avoid the problems discussed above.

According to the invention, the problem concerning the method is solved by a process for the detection and localization of diffuse reflecting coatings on a translucent pane through the use of an optical sensor array that contains a receiving unit.

BRIEF DESCRIPTION OF THE DRAWINGS

Additional particularly advantageous embodiments of the object according to the invention will be explained using the embodiment example represented in the drawings.

DETAILED DESCRIPTION OF THE PREFERRED EMBODIMENT(S)

Figure 1:
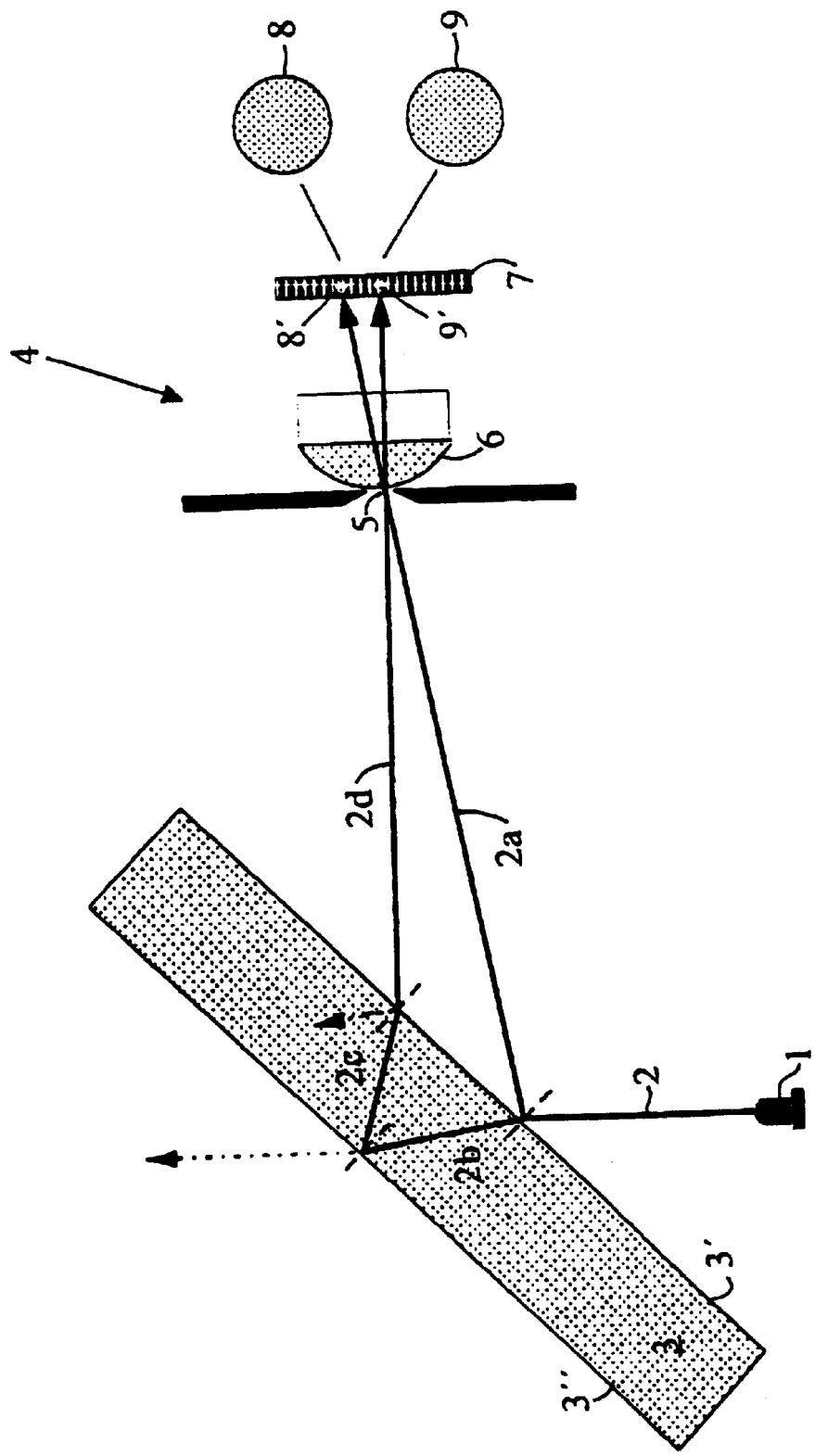
FIG. 1, a schematic representation of a device according to the invention to illustrate the relationships in a pane that is dry and clean on both sides.

As can be seen from FIG. 1, a first part 2a of the beam 2 emitted from a light source 1, such as a light-emitting diode that radiates visible and/or infrared light, and reflected by the surface 3' of the pane 3 called the inner surface below incident on the receiving unit 4. Through this first part 2a of the beam, a first image 8 of the light source 1 is formed at point 8' in the plane of the sensor array 7 by means of display optics including a diaphragm 5 and a collecting lens 6.

A second part 2b of the beam is refracted at the surface 3' and penetrates into the pane 3. At the opposite surface 3" of the pane 3, also called the outer surface below, a part 2c of the beam is reflected, from where, in turn, a part 2d, after another refraction at the first surface 3', arrives at the receiving unit 4 and generates there a second image 9 of the light source 1 at point 9' in the plane of the sensor array 7.

Figure 2:
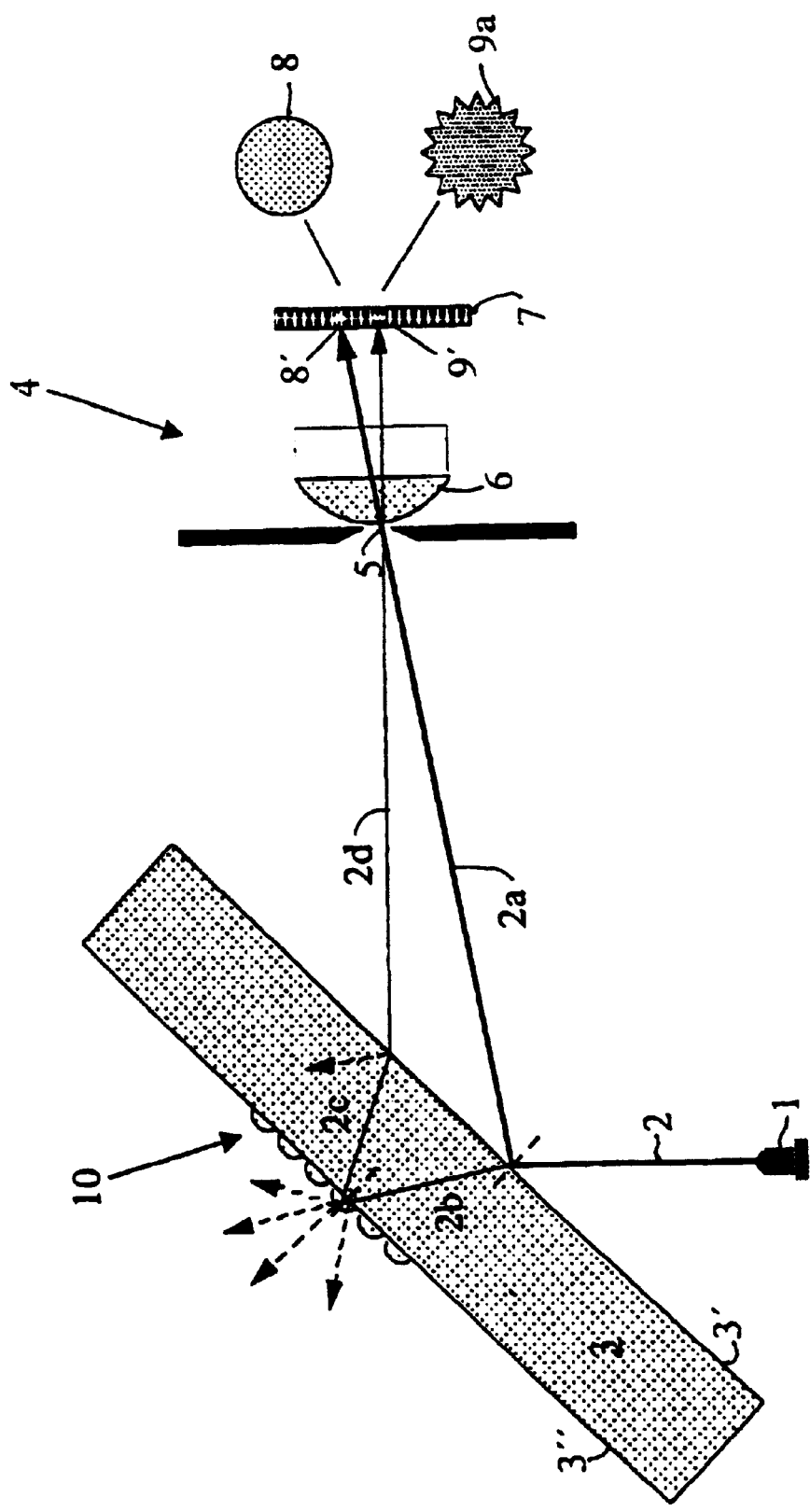
FIG. 2, a schematic representation of a device according to the invention to illustrate the relationship when a coating is present on the outer side of the pane or the side away from the sensor.

As shown by FIG. 2, with a coating 10 on the outer side 3", a sharp image 8 of the light source 1 is received, in contrast, only at point 8', which is generated on the inner side 3' by the part 2a of the beam 2. On the outer side 3" of the pane, the beam 2b that penetrates into the pane is scattered back diffusely or amplified and passes to the outside. The part 2d of the beam 2c that is radiated back diffusely, which still reaches the receiving unit 4 after another refraction at surface 3', is no longer able to generate a sharp image of the light source 1 at point 9', but only a blurred light spot 9a, which can be distinguished unambiguously from the sharp image 9 by means of the intensity profile at its edges, i.e., especially by means of the flat slope of this profile, in the case shown in FIG. 1.

Figure 3:
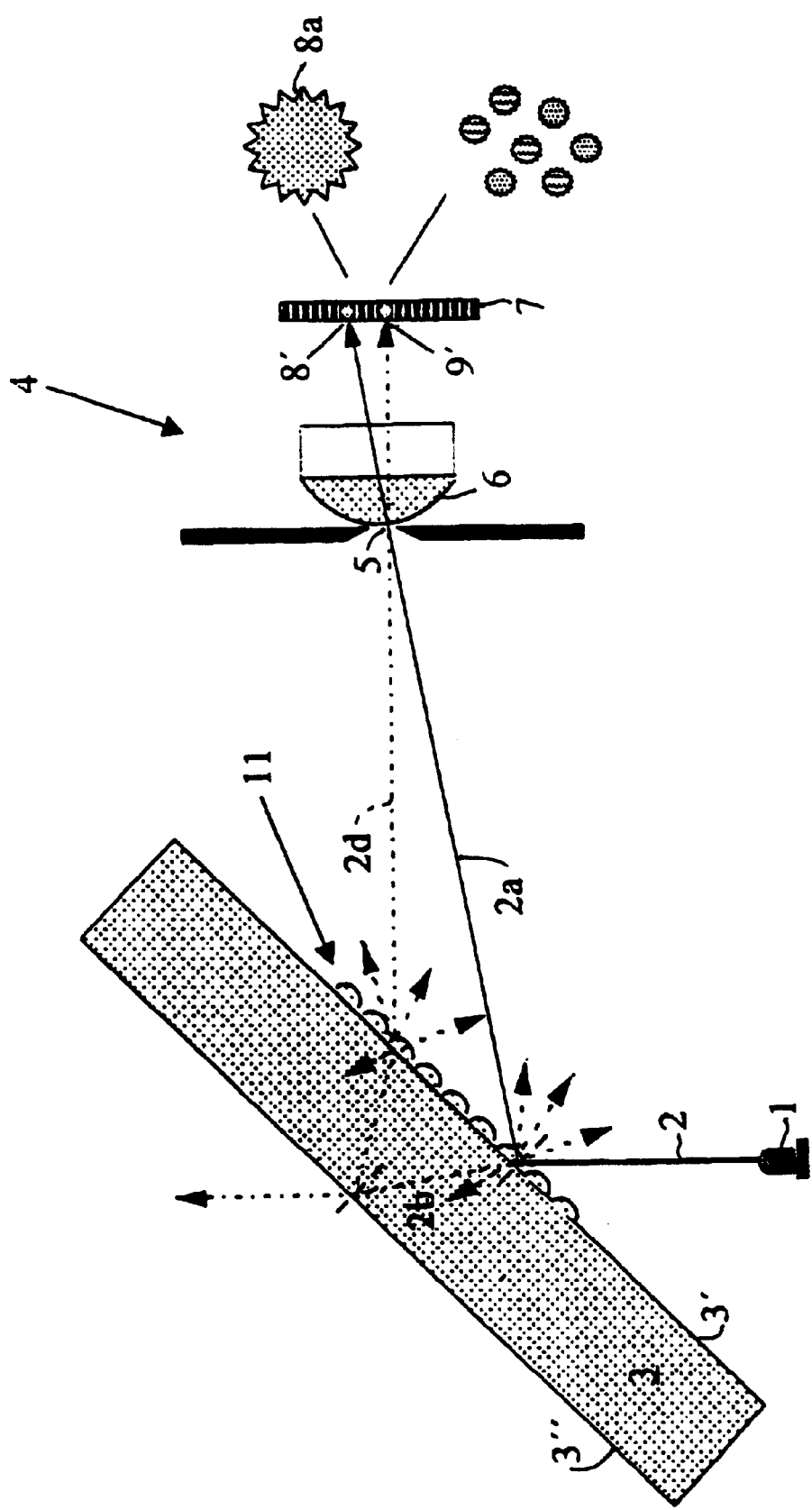
FIG. 3, a schematic representation of a device according to the invention to illustrate the relationship when a coating is present on the inner side of the pane or the side facing the sensor.

The behavior is similar in the situation shown in FIG. 3 of a coating 11 on the inner surface 3', but in this case a diffuse scattering of the beam 2 occurs at this surface 3'. The part 2a of the beam that goes from the inner side 3' of the pane to the receiving unit 4 no longer generates a sharp image of the light source 1 at point 8', but only a blurred light spot 8a, which, like the situation described previously for the light spot 9a FIG. 2, and can be distinguished from the sharp image 8 in the case shown in FIG. 1 by means of the intensity profile at its edges. The part 2d of the beam 2 that reaches the receiving unit 4 after reflection at the outer side 3" of the pane and repeated diffuse scattering at the inner side 3' has lost so much of its original intensity and characteristic direction that no cohesive localizable light spot is even formed at point 9' in the plane of the sensor array 7.

The method according to the invention for evaluating the status of a coating on a pane (3) evaluates the intensity profile currently emitted by the sensor array (7), at which time it is compared with the intensity profile expected at the known points (8',9'), which has been stored as a reference for the state without a coating in order to draw a conclusion about the status of the coating described above from changes in the profile.

When the aforementioned method and device are used in a vehicle, an action control connected after it can trigger various actions on the basis of the existing status of the vehicle, such as applying the air-conditioning system to remove the film of moisture on the inside of the pane and/or the windshield wipers to remove moisture from the exterior side of the pane.

What is claimed is:

1. A method for detecting and localizing coatings on inner and outer surfaces of a translucent pane using a light source and an optical sensor array each positioned adjacent the inner side of the translucent pane, the method comprising:

transmitting a light beam from the light source to the translucent pane;

focusing a first light beam part reflected from the inner surface of the translucent pane to form a first image on the optical sensor array;

focusing a second light beam part reflected from the outer surface of the translucent pane to form a second image on the optical sensor array;

comparing an intensity profile of the first image to a first reference intensity profile indicative of the absence of coatings on the inner surface of the translucent pane;

comparing an intensity profile of the second image to a second reference intensity profile indicative of the absence of coatings on the outer surface of the translucent pane;

determining the absence of coatings on the inner and outer surfaces of the translucent pane if the intensity profile of the first image matches the first reference intensity profile and the intensity profile of the second image matches the second reference intensity profile;

determining the absence of coatings on the inner surface of the translucent pane and the presence of coatings on the outer surface of the translucent pane if the intensity profile of the first image matches the first reference intensity profile and the intensity profile of the second image is different than the second reference intensity profile; and determining the presence of coatings on the inner surface of the translucent pane if the intensity profile of the first image is different than the first reference intensity profile.

2. The method of claim 1 further comprising:

operating an air-conditioning system arranged on the inner side of the translucent pane in response to the presence of coatings on the inner surface of the translucent pane.

3. The method of claim 1 further comprising:

operating a windshield wiper system arranged on the outer side of the translucent pane in response to the presence of coatings on the outer surface of the translucent pane.

4. The method of claim 1 wherein:

the translucent pane is an automobile windshield.

5. The device of claim 1 wherein:

the light source includes a light-emitting diode.

6. The device of claim 1 wherein:

the light beam transmitted by the light source is an infrared light beam.

* * * * *